United States Patent [19]

Fenyes et al.

[11] Patent Number: 4,851,532

[45] Date of Patent: Jul. 25, 1989

[54] IONENE POLYMERIC COMPOSITIONS, THEIR PREPARATION AND USE

[75] Inventors: John D. Pera, Cordova, both of Tenn.

[73] Assignee: Buckman Laboratories, Inc., Memphis, Tenn.

[21] Appl. No.: 930,091

[22] Filed: Nov. 13, 1986

Related U.S. Application Data

[63] Continuation of Ser. No. 735,713, May 20, 1985, abandoned, which is a continuation of Ser. No. 502,025, Jun. 7, 1983, abandoned, which is a continuation-in-part of Ser. No. 280,974, Jul. 7, 1982, abandoned.

[51] Int. Cl.$^4$ .................... A61K 31/50; C07D 403/06
[52] U.S. Cl. ........................................ 544/357; 8/188; 8/567; 8/606; 71/92; 514/252; 514/253; 544/360; 544/401
[58] Field of Search ............... 544/357, 360, 401, 371

[56] References Cited

U.S. PATENT DOCUMENTS

| | | |
|---|---|---|
| 3,917,817 | 11/1975 | Vanlerberghe et al. |
| 4,271,053 | 6/1981 | Kelsey et al. ................... 544/358 X |
| 4,325,940 | 4/1982 | Green et al. ...................... 544/86 X |
| 4,374,244 | 2/1983 | Green et al. ...................... 544/86 X |

Primary Examiner—Anton H. Sutto
Assistant Examiner—Mark W. Noel
Attorney, Agent, or Firm—Finnegan, Henderson, Farabow, Garrett & Dunner

[57] ABSTRACT

Novel capped polymeric quaternary ammonium compositions formed by reacting ionene type polymers with tertiary amines are useful as microbicides, corrosion inhibitors, debonding agents, flocculants, softeners, plant growth regulators, and demulsifiers.

6 Claims, No Drawings

IONENE POLYMERIC COMPOSITIONS, THEIR PREPARATION AND USE

This application is a continuation of application Ser. No. 735,713, filed May 20, 1986 which is a continuation of parent application Ser. No. 502,025 filed June 7, 1983, which is a continuation-in-part of parent application Ser. No. 280,974, filed July 7, 1982, now abandoned.

This invention relates to novel ionene type polymeric compositions and to their uses as microbicides, plant growth regulators, corrosion inhibitors, debonding agents in the manufacture of fluff pulp, softeners, antistatic agents, demulsifiers, and to improve dyeability and color fastness in textiles and paper.

The novel ionene polymeric compositions have the structure:

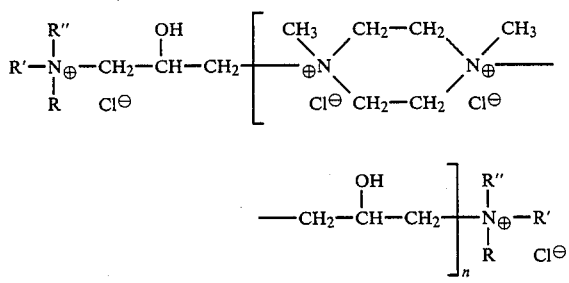

wherein R is methyl, ethyl, propyl, butyl, hydroxyethyl, or hydroxypropyl; characterized in that R, R', and R" are identical when R is ehtyl, propyl, butyl, hydroxy or hydroxypropyl and when R is methyl, R' is methyl or an alkyl group containing 5 to 22 carbon atoms having 0 to 2 carbon to carbon double bonds, cyclohexyl, benzyl or phenyl; and R" is an alkyl group containing 5 to 22 carbon atoms having 0 to 2 carbon to carbon double bonds and characterized further in that R, R', and R" may form a pyridyl group and n is an odd number from 1 to 201.

The polymers of this invention are prepared using a two-stage procedure. In the first stage X moles of N,N'-dimethyl-N,N'-bis(3-chloro-2-hydroxypropyl)-piperazinium dichloride is reacted at an elevated temperature in the presence of water with X-1 moles of a ditertiary amine. We have found suitable reaction temperatures and times may vary from about 80° to 105° C. and from 1 to 30 hours. As used herein and in the appending claims, X is an integer varying from 2 to 101.

In the second stage, one mole of the precursor obtained in the first stage is reacted in the presence of water or a solvent with two moles of a monotertiary amine at a temperature varying from about 25° to 110° C. for a period varying from about 1 to 30 hours. Suitable solvents are water soluble lower alcohols and other polar compounds. The molecular weight of the precursor is calculated by multiplying X times the molecular weight of the chlorohydroxypropyl substituted ditertiary amine used and adding X-1 times the molecular weight of the second ditertiary amine.

The first stage of the process involves the reaction of an α,ω-ditertiary amine with an α,ω-dihalogenated alkyl compound. This reaction is known in the chemical literature as a Menschutkin Reaction and is used to prepare relatively low molecular weight polymers which are polymeric quaternary ammonium compounds known as ionene polymers. The molecular weights of these linear ionenes are generally about 50,000 or less.

The polymer chain length can be controlled by using the method of manufacture described in this invention. When two moles of the α,ω-dihalo compound (X moles) are reacted with one mole (X-1 mole) of the ditertiary amine, a very short polymer is formed. When the designation A is used for the dihalo compound and B for the ditertiary amine the polymer could then be designated A-B-A. When 5 moles of A and 4 moles of B are reacted the precursor then is A-B-A-B-A-B-A-B-A. The same general scheme can be used to a maximum of about 101 for A and 100 for B. Regardless of the number of moles of A and B used, there will be a halogen at either end of the precursor polymer, This precursor is then reacted with a monotertiary maine in the second stage to "cap" the ionene with additional quaternary ammonium groups. The nature of the tertiary amine and the length of the precursor polymer chain will determine the properties of the polymers of this invention and allow for the variation of hydrophilic and hydrophobic properties.

N,N'-dimethyl-N,N'-bis(3-chloro-2-hydroxypropyl)-piperazinium dichloride used in the first stage is prepared by reacting the dihydrochloride salt of N,N'-dimethylpiperazine with two moles of epichlorodhydrin. The α,ω-dichlorodiquaternary ammonium compound so obtained is then reacted with the free base N,N'-dimethylpiperazine to produce the ionene polymers of the first stage.

The monotertiary amines used in the second stage to cap the ionene polymers include alphatic, alicyclic, alkylaromatic, aromatic and heterocyclic amines. The aliphatic groups may contain one or more carbon to carbon double bonds and may be substituted with hydroxyl groups. Examples of these amines are N,N-dimethylmethanamine (also known as trimethylamine), N,N-diethylethanamine (also known as triethylamine), N,N-dimethyl-l-octadecanamine (also known as (dimethylstearylamine), N,N-dimethyl-l-octadecenamine (also known as dimethyloleylamine), N,N-dimethyl-l-decanamine (also known as dimethylcaprylamine), N,N-dimethyl-l-dodecanamine (also known as dimethyllaurylamine), N,N-dimethyll-tetradecanamine (also known as dimethylmyristylamine), N,N-dimethyl-l-hexadecanamine (also known as dimethylpalmitylamine), N-methyl-N-octadecyl-l-octadecanamine (also known as methyldistearylamine), N-decyl,N-methyl-l-decanamine (also known as didecylmethylamine), methyldicocoamine, methyl di-hydrogenated tallow amine, 1-chloro-3-(dimethylamino)-2-propanol, N,N-dimethylbenzeamine (also known as dimethylaniline), pyridine, N,N-dimethylbenzenemethanamine (also known as dimethylbenzylamine), 2,2',2"-nitrilotrisethanol (also known as triethanolamine), 2-(dimethylamino)ethanol, 1,1',1"-nitrolotris-2-propanol (also known as triisopropanolamine), N,N-bis(l-methylethyl)-2-propanamine, and N,N-dimethylcyclohexylamine.

Ionene-type polymers which are prepared by reacting ditertiary amines with dihalo compounds are typically products with relatively low molecular weights. These products may be effective for controlling microorganisms, but their use as plant growth regulators is limited. The most versatile cationic polymers are the polyethylenimines which can be manufactured in various molecular weight ranges by the selection of different catalysts and the use of cross-linking reagents. None of the polyethylenimines are good microbicides or plant growth regulators.

The degradative effect of microorganisms on organic materials is well known. Elimination or inhibition of growth of algae, bacteria, and fungi has been the objective of a large number of research projects and patents. Quaternary ammonium compounds and ionene polymers have found utility for the treatment of water used in various commercial and industrial cooling systems and in swimming pools. We have found that the cationic polymers of this invention are effective against algae, bacteria, and fungi in water systems even when used in very low concentrations.

A very important aspect of our invention, if not the most important, is that the compositions disclosed herein exhibit remarkable properties as plant growth regulators. As to the importance of this feature in reference to the economy in general and to agriculture in particular, the following comments are pertinent. In 1975 the National Academy of Sciences pointed out that the use of plant-growth regulators may be the cause of the most important quantitative yields yet achieved in agriculture. Plant-growth regulators are used to modify the crop by changing the rate, pattern, or both, of the crop's response to the internal and external factors that govern all stages of crop development from germination through vegetative growth, reproductive development, maturity, and senescense, as well as post-harvest preservation.

Plant growth regulators other than nutrients are usually organic compounds, either natural or synthetic, and are applied directly to a plant to alter its life process or structure in some beneficial way so as to enhance yield, improve quality, or facilitate harvesting.

When the polymers of our invention are used as plant growth regulators generally best results are obtained when about 2 oz. to 32 oz. of the ionene polymeric compositions are applied per acre of the crop plant, although beneficial results are obtained when as little as 1 oz. and as much as 64 oz. of the ionene polymeric compositions are applied per acre. More than 64 oz. per acre is generally not desirable because of diminished improvement and increased costs. It will be appreciated that the optimum amount depends on many factors such as density of plants, type or variety of plants, efficiency of application, etc. Rainfall within a few hours of application is deleterious and to the extent possible, treatment should take place when rainfall is not iminent.

The plant growth regulators of our invention can be used successfully on a wide variety of plant species. These regulators are of special value to agriculturally important crops, such as cotton, the grains, the legumes, and numerous vegetable and fruit crops. In addition, these regulators can also be used on ornamentals, house plants, and other plants grown principally or solely for their decorative value.

The ionene polymers of this invention are soluble in water or other polar solvents such as alcohols, glycols and dimethylformamide. Concentrations which are suitable for control of microorganisms vary from 0.5 to to 500 ppm based on the weight of the water being treated. For control of corrosion in aqueous systems, concentrations of 0.5 to 500 ppm based on the weight of water treated are suitable with a preferred concentration range of 0.5 to 50 ppm. As a debonding agent for cellulose pulp, the ionene polymers of this invention are used in amounts varying from 0.1 to 2.0 parts per 100 parts of cellulose pulp fiber based on the dry weight of the fiber. The softening of textiles, paper or cellulose pulp sheets is achieved with these polymers in amounts of 0.1 to 1.0 part per 100 parts of textile fabric, paper, or cellulose pulp based on the dry weight of material treated.

As a demulsifier to break oil-in-water or water-in-oil emulsions, concentrations of 0.5 to 500 ppm based on the weight of the emulsion are suitable. When used as antistatic agents for textile fabrics, plastics, or paper, suitable quantities of the polymers of this invention may vary from 0.1 to 2.0 parts per 100 parts of material treated. To improve the dyeability and color fastness in textiles and paper, suitable polymer concentrations range from 0.05 to 1.0 part per 100 parts of dry textile fabric or dry paper.

It is, therefore, a principal object of our invention to provide novel ionene polymeric compositions.

It is another object of our invention to provide a method for the control of the growth and development of plants.

It is yet another object of our invention to provide methods for controlling the growth of algae, bacteria, and fungi in aqueous systems.

These and other objects and advantages of the novel compositions and methods of this invention will become apparent as the description proceeds.

In order to disclose the nature of the present invention still more clearly, the following illustrative examples will be given. It is to be understood, however, that the invention is not to be limited to the specific conditions or details set forth in these examples except insofar as such limitations are specified in the appended claims.

EXAMPLE 1

Preparation of
N,N'-dimethyl-N,N'-bis(3-chloro-2-hydroxypropyl) piperazinium dichloride (Precursor A)

A 5000 mL four-neck round-bottom flask equipped with a reflux condenser, mechanical stirrer, thermometer and a dropping funnel was charged with 1198.5 (5.0 moles) of a 47.6 percent aqueous solution of 1,4-dimethylpiperazine. The solution was cooled by means of an ice-water bath and 985.5 g (10.0 moles) of 37 percent hydrochloric acid was added at such a rate as to keep the temperature below 45° C. To the well-agitated 1,4-dimethylpiperazine dihydrochloride solution so obtained, 925.2 g (10.0 moles) of epichlorohydrin was added slowly, again at such a rate as to keep the temperature below 45° C. After the addition was completed, the temperature of the reaction mixture was raised to between 60 and 70° C. for 30 minutes, followed by another hour at 100° C. A 59.8 percent solution of N,N'-dimethyl-N,N'-bis-(3-chloro-2-hydroxypropyl)-piperazinium dichloride was obtained.

EXAMPLES 2 to 5

Various quantities of the 59.8 percent aqueous solution of N,N'-dimethylN,N'-bis(3-chloro-2-hydroxypropyl)piperazinium dichloride (Precursor A) prepared in Example 1 and varying quantities of 1,4-dimethylpiperazine were refluxed for 18 hours while being stirred vigorously. The reaction products, polyquaternary ammonium salts, were obtained as aqueous solutions having total solids content as indicated in Table 1.

TABLE 1

| Example | Precursor Prepared | Precursor A to 1,4-Dimethylpiperazine Moles Ratio | Solids Content Percent |
|---|---|---|---|
| 2 | B | 2 to 1 | 57.8 |
| 3 | C | 3 to 2 | 57.3 |
| 4 | D | 4 to 3 | 57.1 |
| 5 | E | 5 to 4 | 57.0 |

EXAMPLES 6 to 13

Various quantities of the 59.8 percent aqueous solution of Precursor A of Example 1 were reacted with a number of tertiary amines at a mole ratio of 2 to 1 of tertiary amine to Precursor A. These reactions are given below in Table 2.

TABLE 2

| Example | Tertiary Amine | Time of Reaction Hours | Solids Content Percent |
|---|---|---|---|
| 6 | N,N—dimethyl-1-dodecanamine | 6 | 76.2 |
| 7 | N,N—dimethyl-1-tetradecanamine | 6 | 50.0* |
| 8 | N,N—dimethyl-1-hexadecanamine | 6 | 50.0* |
| 9 | N,N—dimethyl-1-octadecanamine | 8 | 25.0* |
| 10 | 2,2′,2″-nitrilotrisethanol | 4 | 72.9 |
| 11 | pyridine | 18 | 66.0 |
| 12 | 1,1′,1″-nitrilotris-2-propanol | 6 | 75.0 |
| 13 | N—methylpiperidine | 8 | 50.0* |

*In these reactions, enough water was used to give solutions containing either 25% or 50% of the product.

EXAMPLES 14 to 20

Various quantities of the 57.8 percent aqueous solution of Precursor B of Example 2 were reacted at reflux temperature with a number of tertiary amines at a mole ratio of 2 to 1 of tertiary amine to Precursor B. These reactions are given below in Table 3.

TABLE 3

| Example | Tertiary Amine | Time of Reaction Hours | Solids Content Percent |
|---|---|---|---|
| 14 | N,N—dimethyl-1-dodecanamine | 6 | 66.8 |
| 15 | N,N—dimethyl-1-tetradecanamine | 6 | 50.0* |
| 16 | N,N—dimethyl-1-hexadecanamine | 6 | 50.0* |
| 17 | N,N—dimethyl-1-octadecanamine | 10 | 25.0** |
| 18 | 2,2′,2″nitrilotrisethanol | 4 | 64.4 |
| 19 | pyridine | 18 | 68.5 |
| 20 | 1,1′,1″nitrolotris-2-propanol | 6 | 66.5 |
| 21 | N—methylpiperidine | 8 | 50.0* |

*In these reactions, enough water was used to give products containing 50.0% solids.
**In this reaction, enough propylene glycol was used to give products containing 25.0% solids.

EXAMPLES 22 to 29

Various quantities of the 57.3 percent aqueous solutions of Precursor C of Example 3 were treated at reflux temperature with a number of tertiary amines at a mole ratio of 2 to 1 tertiary amine to Precursor C. These reactions are included in Table 4.

TABLE 4

| Example | Tertiary Amine | Time of Reaction Hours | Solids Content Percent |
|---|---|---|---|
| 22 | N,N—dimethyl-1-dodecanamine | 6 | 53.9 |
| 23 | N,N—dimethyl-1-tetradecanamine | 6 | 64.6 |
| 24 | N,N—dimethyl-1-hexadecanamine | 6 | 65.3 |
| 25 | N,N—dimethyl-1-octadecanamine | 10 | 25.0** |
| 26 | 2,2′,2″-nitrilotrisethanol | 4 | 65.3 |
| 27 | pyridine | 18 | 59.8 |
| 28 | 1,1′,1″-nitrilotris-2-propanol | 6 | 63.3 |
| 29 | N—methylpiperidine | 8 | 50.0* |

*In this reaction, enough water was used to give a product containing 50.0% solids.
*In this reaction, enough propylene glycol was used to give a product containing 25.0% solids.

EXAMPLES 30 to 37

Various quantities of the 57.1 percent aqueous solution of Precursor D of Example 4 were treated at reflux temperature with a number of tertiary amines at a mole ratio of 2 to 1 of tertiary amine to Precursor D. These reactions are included in Table 5.

TABLE 5

| Example | Tertiary Amine | Time of Reaction Hours | Solids Content Percent |
|---|---|---|---|
| 30 | N,N—dimethyl-1-dodecanamine | 6 | 62.9 |
| 31 | N,N—dimethyl-1-tetradecanamine | 6 | 62.7 |
| 32 | N,N—dimethyl-1-hexadecanamine | 6 | 63.3 |
| 33 | N,N—dimethyl-1-octadecanamine | 10 | 25.0** |
| 34 | 2,2′,2″-nitrilotrisethanol | 4 | 60.7 |
| 35 | pyridine | 18 | 59.0 |
| 36 | 1,1′,1″-nitrilotris-2-propanol | 6 | 61.7 |
| 37 | N—methylpiperidine | 8 | 50.0* |

*In this reaction, enough water was used to give a product containing 50.0% solids.
*In this reaction, enough propylene glycol was used to give a product containing 25.0% solids.

EXAMPLES 38 to 45

Various quantities of the 57.0 percent aqueous solution of Precursor E of Example 5 were reacted with a number of tertiary amines at a mole ratio of 2 to 1 of tertiary amine to Precursor E. These reactions are given below in Table 6.

TABLE 6

| Example | Tertiary Amine | Time of Reaction Hours | Solids Content Percent |
|---|---|---|---|
| 38 | N,N—dimethyl-1-dodecanamine | 6 | 50.0* |
| 39 | N,N—dimethyl-1-tetradecanamine | 6 | 50.0* |
| 40 | N,N—dimethyl-1-hexadecanamine | 6 | 50.0* |
| 41 | N,N—dimethyl-1-octadecanamine | 10 | 25.0** |
| 42 | 2,2',2"-nitrilo-trisethanol | 4 | 50.0* |
| 43 | pyridine | 16 | 50.0* |
| 44 | 1,1',1"-nitrilotris-2-propanol | 5 | 50.0* |
| 45 | N—methylpiperidine | 8 | 50.0* |

*In this reaction, enough water was used to give a product containing 25.0 percent solids.
**In this reaction, enough propylene glycol was used to give a product containing 25.0 percent solids

EXAMPLE 46

The effect of the novel ionene type polymeric compositions described in the preceding examples on the percentage kill of the bacterium *Enterobacter aerogenes* was determined using the method described in U.S. Pat. No. 2,881,070 with the modification described in U.S. Pat. No. 4,054,542. The results are included in Table 7.

TABLE 7

| | Concentration in parts per million required for 80 percent kill or greater of *Enterobacter aerogenes* in a basal salt substrate after 18 hours contact | | |
|---|---|---|---|
| Ionene polymer from examples | pH 6.0–6.5 | pH 7.0–7.5 | pH 8.0–8.5 |
| 1 | 1.0 | — | — |
| 2 | — | 4.0 | 4.0 |
| 4 | — | 2.0 | 4.0 |
| 5 | 4.0 | 4.0 | — |
| 7 | 4.0 | 4.0 | — |
| 8 | 4.0 | 4.0 | — |
| 13 | 2.0 | 2.0 | 2.0 |
| 14 | 2.0 | 2.0 | 2.0 |
| 15 | 2.0 | 2.0 | 2.0 |
| 20 | — | 1.0–2.0 | 0.5 |
| 21 | — | 1.0–2.0 | 0.5 |
| 22 | — | 1.0–2.0 | 0.5 |
| 27 | 2.0 | 1.0–2.0 | 2.0 |
| 28 | 2.0 | 1.0–2.0 | 2.0 |
| 29 | 2.0 | 1.0–2.0 | 2.0 |

EXAMPLE 47

The effect of some of the ionene type polymeric composition described in the preceding examples on the inhibition of algae *Chlorella pyrenoidosa*, *Chlorococcum hypnosporum*, and *Phormidium inundatum* was determined using the procedure described in Example 2 of U.S. Pat. No. 3,771,989. The results are included in Table 8. Observations of growth were made after 28 days on the basis of the following Key:
4 = Excellent
3 = Good
2 = Poor
1 = Very poor, scant, questionable
0 = No growth

TABLE 8

| | Concentration in parts per million required for inhibition of growth after 28 days | | |
|---|---|---|---|
| Ionene polymer from examples | *Chlorella pyrenoidosa* | *Chlorococcum hypnosporum* | *Phormidium inundatum* |
| 2 | 8.0 | 8.0 | — |
| 3 | 4.0 | 4.0–8.0 | — |
| 4 | 1.0–2.0 | — | — |
| 5 | 2.0 | 2.0 | 4.0 |
| 7 | 2.0 | 4.0 | — |
| 8 | 2.0 | 4.0 | 4.0 |
| 13 | 2.0–4.0 | 4.0 | — |
| 14 | 2.0–4.0 | 4.0 | — |
| 15 | 2.0–4.0 | 4.0 | 8.0 |
| 20 | 2.0 | 2.0 | 8.0 |
| 21 | 2.0 | 2.0 | 8.0 |
| 22 | 2.0 | 2.0 | 8.0 |

EXAMPLE 48

The ionene-type polymers of this invention were used in the treatment of wet bleached pine kraft pulp in the form of an aqueous slurry with a pulp consistency of 0.5 percent. Handsheets were formed from the pulp on a laboratory handsheet machine to produce 20 cm × 20 cm pulp sheets with basis weights of 120 g/m². After the sheets were formed, pressed and dried by the standard procedure, the debonding effect was evaluated by determining the fiber-to-fiber internal bonding strength of these sheets by means of a Scott Internal Bond Tester as described in TAPPI UM-403. The debonding effect was expressed as a percentage factor calculated as follows:

Internal Bond Factor =

$$\frac{(\text{Internal Bond of Treated Pulp Sheet}) \times 100}{\text{Internal Bond of Untreated Pulp Sheet}}$$

Thus, the untreated pulp would have an Internal Bond Factor of 100 and debonded pulp would have an Internal Bond Factor below 100; the lower this factor, the greater the degree of debonding achieved.

Table 9 shows the results obtained with the ionene polymers when they were evaluated by the indicated test method. Treatment rates are in weight percent based on the dry weight of pulp.

TABLE 9

| Example | Treatment Rate Percent | Internal Bond Factor |
|---|---|---|
| 12 | 0.5 | 82 |
| 13 | 0.5 | 78 |

These results show that the ionene polymers of this invention are good debonding agents, reducing the internal bond strength to as low as 48 percent of the strength of the original untreated pulp.

Compositions of our invention have been found to produce a variety of plant growth regulator responses when applied to cotton, leguminous crop plants, specifically soybean and other crop plants.

The terms "plant growth regulant effect", "plant growth regulation", or words to that effect, are used in this specification and in the claims to means the causation by the chemicals of the present invention, of a variety of plant responses which achieve a promotion, inhibition or modification of any plant physiological or morphological process. It should additionally be recognized that various plant responses may also result from a combination or sequence of both physiological and morphological factors.

The plant growth regulant effects which may be produced in leguminous plants, specifically soybean, using the compositions of the present invention are probably most readily observable as changed in the size, shape, color or texture of the treated plant or any of its parts. Similarly, changes in the quantity of the plant fruit or flowers are also quite apparent from visual inspection. The foregoing changes may be characterized as an acceleration or retardation of plant growth, stature reduction, leaf or canopy alternation, increased branching, tillering, terminal inhibition, increased flowering or fruit set, increased root growth, axillary bud development or inhibition delayed budding, defoliation, desiccation, delayed senescence, prolongated dormancy, increased cold hardiness, delayed or accelerated ripening, and the like.

It is to be understood that each response may occur in conjunction with other responses, but may also occur separately. For example, depending upon various factors realized by those skilled in the art to effect activity, the data illustrated below demonstrate that the compounds of the present invention sometimes alter the leaf morphology even though the plants are not reduced in stature.

Alteration of the leaf morphology of leguminous plants is important because leguminous plants have canopies that effectively inhibit sunlight from reaching the lower leaves. For example, only about 50% of a soybean plant's leaves intercept light for photosynthesis. Approximately 85% of the light is absorbed by the outer layer of leaves. Many researchers feel that by altering the morphology of the leaves such that the canopy is altered, light may fall more deeply into the canopy, and yields could be increased. Thus, it would be highly beneficial if a method was found whereby the leaves of such plants could be altered such that a greater number of leaves could be illuminated.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatures and are more resistant to pest infestations and to lodging. Reduction in the maturation rate on portions of a crop permits an extended harvest period to peak yield and more efficient use of subsequent crop processing equipment. Suppression of vegetative growth at the appropriate stage of the plant's development may result in increased energy available for utilization in reproductive development so that, for example, more fruit or larger fruit is formed.

It is to be understood that the regulation of desirable crop plant in accordance with the instant invention does not include the total inhibition or the killing of such plants. Although phytotoxic amounts of the materials disclosed herein might be employed to exert a herbicidal (killing) action, it is contemplated here to employ only plant regulating amounts of such meterials in order to modify the normal sequential development of the treated plant to agricultural maturity. The application of a plant regulating amount may be applied to plants in sequence at various stage of the plant's development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transistory effect is sought.

In accordance with this invention, it has been found that desirable modification of leguminous crop plants is achieved by applying the above-described plant regulants to the "plant" or plant "habitat". The term "plant" is understood herein to include the seeds, emerging seedlings, roots, stems, leaves, flowers, fruits, or other plant parts. The term "habitat" is understood herein to means the environment of the plant such as the plant growing medium, e.g., the soil.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents. Thus, the active ingredient can be used with an adjuvant such as a solvent liquid of organic origin, water, a wetting agent, dispersing agent or emulsifying agent or any suitable combination of these.

Typical liquid diluents include water, alcohols, glycols and the like. The plant growth regulating compositions of this invention usually contain one or more surface-active agents in amounts sufficient to render a given composition readily dispersible in water.

Laboratory tests described in the following Examples 49 and 50 are designed to demonstrate that the candidate growth regulators are active by showing whether they effect ethylene evolution, $CO_2$ fixation, and $O_2$ evolution. The fact that the polymers of this invention alter these normal physiological functions of plants proves they are growth regulators.

EXAMPLE 49

The polymer of example 45 shows outstanding increased in ethylene evolution on soybean and cotton and this polymer is an excellent fruit ripener, cotton boll opener, flower inducer, etc. Reduced ethylene production, as with the polymers of Examples 38, 39, and 40, decreases flowering, ripening, and vegetative growth, etc.

The effect of some of the novel ionene-type polymeric compositions described in the preceding examples on the percent Oxygen Evolution and $^{14}CO_2$ Uptake by Leaf Discs was determined according to the following experiment.

Cotton and soybean seeds from a single parent plant were germinated in vermiculite moistened with tap water in a controlled environment chamber. Eight to ten days after germination, eight 1-cm. diameter discs were cut with a cork borer from visually equivalent, fully expanded leaves and placed into a 30-ml. glass vial. A small amount of degassed 0.1M phosphate buffer (pH 6.4) was immediately added to each vial. This solution was infiltrated into the leaf discs by applying an intermittent vacuum of 50 to 75 mm. Hg, gently decanted, and a fresh 25.0-ml. aliquot of the same solution and a magnetic stirring bar were added. A Clark oxygen electrode mounted in a rubber stopper was immediately inserted into each vial, from which air bubbles escaped through a groove along the outside of the stopper. The vial-electrode unit was placed in a Plexiglas water jacket over a magnetic stirrer, which was then started.

After equilibration in dim light after 10 minutes, cool white and fluorescent lamps were switched on at either side of the water jacket. Four such vial electrode units were used simultaneously.

This apparatus made it possible to examine aspects of leaf disc activity by measuring net oxygen evolution and net carbon dioxide uptake. Estimates of apparent $CO_2$ uptake could be made using this same apparatus, with the injection of 5umole of $NaH^{14}CO_3$ to the buffered solution immediately after each vial was sealed. Following the measurement of $O_2$ evolution, the leaf discs were rinsed in tap water, placed into centrifuge tubes containing 2 ml. of 5% (w/v) trichloroacetic acid in ethanol and 0.1 g. of activated charcoal, and covered with Parafilm. After incubation at 21 to 24° C. for 48 hr., the samples were centrifuged at 1000 rcf (relative centrifugal force, or 13000 X G) for 10 minutes. A 0.5-ml. aliquot of the supernatant was added to a counting vial containing 20 ml of liquid scintillator (4.0 g. PPO (2,5-diphenyloxazole), 0.1 g. POPOP (1,4-bis[2-(5-phenyloxazolyl)]benzene), in 700 ml. toluene and 300 ml. absolute ethanol) for counting in a liquid scintillation system. The count data obtained were interpreted as residual $^{14}C$ activity fixed in ethanolic TCA-stable forms. The effect of plant growth regulators on $O_2$ evolution and $^{14}CO_2$ fixation was measured by adding these chemicals in a 0.25-ml. aliquot to the reaction medium at the beginning of the 10-minute equilibration.

The results of these tests using the polymers listed are included in Table 10.

TABLE 10

| Ionene polymer from examples | On Cotton | | | | | |
|---|---|---|---|---|---|---|
| | $CO_2$ Fixation | | | $O_2$ Evolution | | |
| | 50 ppm | 100 ppm | 250 ppm | 50 ppm | 100 ppm | 250 ppm |
| 38 | −7 | −17 | −17 | +49 | +12 | +10 |
| 39 | −7 | −8 | −17 | +48 | +12 | +10 |
| 40 | −7 | −17 | −15 | +45 | +14 | +11 |
| 45 | +3 | −2 | +37 | −11 | −16 | −26 |

| | On Soybean | | | | | |
|---|---|---|---|---|---|---|
| | 25 ppm | 50 ppm | 100 ppm | 25 ppm | 50 ppm | 100 ppm |
| 38 | +63 | +70 | +43 | −45 | −38 | −66 |
| 39 | +65 | +70 | +43 | −45 | −38 | −66 |
| 40 | +65 | +69 | +42 | −44 | −37 | −65 |
| 45 | −6 | −3 | +10 | −25 | −14 | −45 |

EXAMPLE 50

The increased $CO_2$ fixation and increased $O_2$ evolution with the polymers of Examples 38, 39, and 40 have an effect on the nutritional uptake within the plant such as the assimilation of nitrogen for vegetative growth and potassium for fruit maturation.

The effect of some of the novel ionene type polymeric compositions described in the preceding examples on the percent Ethylene Evolution was determined by the Leaf Disc Method as follows:

Leaf discs as obtained for the $O_2$—$^{14}CO_2$ tests were submerged in experimental test solution for approximately 20 minutes after which time they were rinsed with deionized water and rapidly blotted and placed into a 4-cc vial and sealed with a serum stopper. After 1, 8, and 24 hours, samples were removed from the vial for ethylene determination. After each sampling time $N_2$ gas was used to flush the vial before setting aside for the next sampling time. Ethylene analysis was made by injecting 1-cc samples from the vials into a Perkin-Elmer gas chromatograph equipped with a 6-ft. Pora-Pak Q, 80 to 100 mesh column. Detector response to standard ethylene gas was used for reference standards. The ethylene was calculated as ml. ethylene/liter $cm^{-2}$ $hr^{-1}$, and comparisons made as percentage changes from non-treatments, positive or negative.

The results of this test using the polymers listed are included in Table 11.

TABLE 11

| Ionene polymers from examples | Ethylene percent increase over control on cotton | | |
|---|---|---|---|
| | 50 ppm | 100 ppm | 250 ppm |
| 38 | +15 | −25 | −10 |
| 39 | +15 | −22 | −10 |
| 40 | +17 | −21 | −10 |
| 45 | −19 | +90 | +129 |

| | Ethylene percent increase over control on soybean | | |
|---|---|---|---|
| | 25 ppm | 50 ppm | 100 ppm |
| 38 | −46 | −25 | −38 |
| 39 | −43 | −22 | −36 |
| 40 | −43 | −27 | −37 |
| 45 | +70 | +70 | +250 |

The invention having thus been described, what is claimed and desired to be secured by Letters Patent is:

1. An ionene polymeric composition having the structure

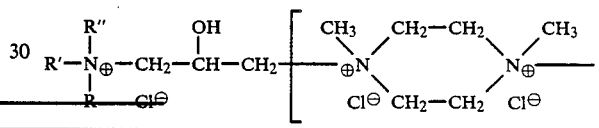

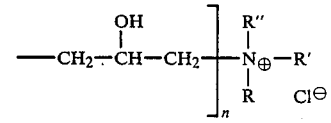

wherein R is methyl, ethyl, propyl, butyl, hydroxyethyl, or hydroxypropyl; characterized in that R, R', and R" are identical when R is ethyl, propyl, butyl, hydroxyethyl or hydroxypropyl and when R is methyl, R' is methyl or an alkyl group having 5 to 22 carbon atoms and also having 0 to 2 carbon to carbon double bonds, cyclohexyl, benzyl or phenyl; and R" is an alkyl group having 5 to 22 carbon atoms and also having 0 to 2 carbon to carbon double bonds and characterized further in that R, R', and R" may form a pyridyl group and n is an odd number from 1 to 201.

2. The ionene polymeric composition of claim 1 wherein R and R' are methyl and R'' is decyl.

3. The ionene polymeric composition of claim 1 wherein R and R' are methyl and R'' is dodecyl.

4. The ionene polymeric composition of claim 1 wherein R and R' are methyl and R'' is tetradecyl.

5. The ionene polymeric composition of claim 1 wherein R and R' are methyl and R'' is hexadecyl.

6. The ionene polymeric composition of claim 1 wherein R is methyl and R' and R'' are decyl.

* * * * *

UNITED STATES PATENT AND TRADEMARK OFFICE
CERTIFICATE OF CORRECTION

PATENT NO. : 4,851,532

DATED : July 25, 1989

INVENTOR(S) : Joseph G. Fenyes et al.

It is certified that error appears in the above-identified patent and that said Letters Patent is hereby corrected as shown below:

On the title page

In the section entitled "Inventors", before "John" insert --Joseph G. Fenyes, Germantown and--.

In the section entitled "Assignee", after "Laboratories," insert --Intl.,--.

Signed and Sealed this

Fifth Day of June, 1990

Attest:

HARRY F. MANBECK, JR.

*Attesting Officer*      *Commissioner of Patents and Trademarks*